US00PP14473P39

(12) United States Plant Patent
Pieters

(10) Patent No.: US PP14,473 P3
(45) Date of Patent: Jan. 20, 2004

(54) CHRYSANTHEMUM PLANT NAMED 'GEDI TWO ARE'

(50) Latin Name: *Chrysanthemum morifolium*
Varietal Denomination: Gedi Two Are

(75) Inventor: Dirk Pieters, Staden (BE)

(73) Assignee: Pieters Plant Production, BVBA, Oostnieukerke (BE)

( * ) Notice: Subject to any disclaimer, the term of this patent is extended or adjusted under 35 U.S.C. 154(b) by 0 days.

(21) Appl. No.: 10/137,806

(22) Filed: May 1, 2002

(65) Prior Publication Data

US 2003/0208820 P1 Nov. 6, 2003

(51) Int. Cl.[7] ..... A01H 5/00
(52) U.S. Cl. ..... Plt./298

(58) Field of Search ..... Plt./293, 292, 287, Plt./286, 298

(56) References Cited

U.S. PATENT DOCUMENTS

| | | | | |
|---|---|---|---|---|
| PP9,586 | P | 6/1996 | Fuess | Plt./293 |
| PP10,216 | P | 1/1998 | Pieters | Plt./290 |
| PP11,605 | P | 10/2000 | Pieters | Plt./298 |

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant cultivar characterized by a decorative-type inflorescence, consistent flowering response to short days, blooming consistently after 49 days of short day length, free branching habit, deep red ray florets, a very uniform round growth habit, and a large quantity of blooms per flowering branch.

1 Drawing Sheet

Latin name of the genus and species: The present invention relates to a new and distinct cultivar of Chrysanthemum plant, botanically known as *Chrysanthemum morifolium.*

Variety denomination: The new and distinct Chrysanthemum plant is hereinafter referred to by the cultivar name 'Gedi Two Are.'

BACKGROUND OF THE INVENTION

The new cultivar is a product of hybridization of a female parent, cultivar 'Aldo' (U.S. Plant Pat. No. 10,216), and a male parent, cultivar 'Gedi RA8' (U.S. Plant Pat. No. 11,605). This cultivar was discovered and selected by the inventor in October 1998.

Asexual reproduction of the new cultivar by apical tip cutting and meristem tissue culture was performed in Oxnard, Calif. and has shown that the unique features of this cultivar are stable and reproduced true to type on successive generations.

SUMMARY OF THE INVENTION

The cultivar 'Gedi Two Are' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Gedi Two Are.' These characteristics in combination distinguish 'Gedi Two Are' as a new and distinct Chrysanthemum cultivar:

1. Decorative-type inflorescence,
2. Consistent flowering response to short days, blooming consistently after 49 days of short day length,
3. Free branching habit,
4. Deep red ray florets, 5. Very uniform round growth habit, and
6. Large quantity of blooms per flowering branch.

The new cultivar 'Gedi Two Are' has more ray florets per inflorescence and different color ray florets than the female parent cultivar 'Aldo.' The new cultivar also blooms naturally earlier than 'Aldo.' The new cultivar 'Gedi Two Are' has a different flower type than the male parent cultivar 'Gedi RA8' and is taller and wider than the male parent. The new cultivar also has a wider bloom diameter than 'Gedi RA8' also known as 'Red Alcala'.

In comparison to the commercial variety 'Empire Diablo' (U.S. Plant Pat. No. 9,586), the new cultivar 'Gedi Two Are' blooms naturally two weeks later and has a more flexible plant habit. The new cultivar also has a rounder shape and greater branching than 'Empire Diablo' and has more blooms per flowering branch.

BRIEF DESCRIPTION OF THE PHOTOGRAPH

The photograph shows a plant of 'Gedi Two Are' which was grown in a 6-inch container. One cutting was used in the pot.

DETAILED BOTANICAL DESCRIPTION

In the following description, color references are made to The Royal Horticultural Society Colour Chart except where general terms of ordinary dictionary significance are used. The following observations and measurements describe plants grown in Oxnard, Calif. during the month of December and January. The age of the observed plants is 79 days from a rooted cutting. The growing temperature ranged from 55° to 68° F. at night to 60° to 75 ° F. during the day. Measurements and numerical values represent averages of typical flowering types.

Botanical classification: *Chrysanthemum morifolium* cultivar 'Gedi Two Are'.
Commercial classification: Garden-type Chrysanthemum.
Parentage: Hybridization of *Chrysanthemum morifolium* cultivars 'Aldo' (U.S. Plant Pat. No. 10,216) and 'Gedi RA8' (U.S. Plant Pat. No. 11,605).

PROPAGATION

Time to rooting: 7 to 14 days at approximately 21° C.
Root description: Fine, fibrous.

PLANT

Growth habit: Mounding herbaceous perennial.
Height: Approximately 21 cm.
Spread: Approximately 25 cm.
Growth rate: Moderate.
Branching characteristics: Free Branching.
Length of lateral branches: Approximately 19.5 cm.
Number of leaves per lateral branch: Approximately 19.

FOLIAGE

Leaf:
- *Arrangement.*—Alternate.
- *Average length.*—Approximately 6 cm.
- *Average width.*—Approximately 5.4 cm.
- *Shape of blade.*—Ovate.
- *Apex.*—Cuspidate.
- *Base.*—Attenuate.
- *Attachment.*—Stalked.
- *Margin.*—Palmately lobed.
- *Texture of top surface.*—Lightly pubescent.
- *Texture of bottom surface.*—Lightly pubescent.
- *Color.*—Young foliage upper side: Near 137C. Young foliage under side: Near 138A. Mature foliage upper side: Near 139A. Mature foliage under side: Near 147B. Venation upper side: Near 147D. Venation under side: Near 147C.
- *Venation type.*—Palmately net.

Petiole:
- *Average length.*—Approximately 2.4 cm.
- *Color.*—Nearly 137A.
- *Diameter.*—Approximately 0.3 cm.

BLOOM

Inflorescence:
- *Flowering habit.*—Induced by darkness period greater than 13.5 hours, approximately 49 days of appropriate day length required to induce and develop blooms.
- *Inflorescence form.*—Decorative.
- *Natural flowering season.*—Approximately the middle two weeks of September.
- *Number of inflorescences per lateral branch.*—Approximately 11.
- *Inflorescence diameter.*—Approximately 4.8 cm.
- *Inflorescence depth.*—1.8 cm.
- *Inflorescence longevity on plant.*—Approximately 18 days.
- *Persistence.*—Persistent.

Ray florets:
- *Appearance.*—Matte.
- *Texture.*—Smooth.
- *Average number per flower.*—117.
- *Shape.*—Spatulate.
- *Aspect.*—Flat.
- *Margin.*—Entire.
- *Apex.*—Retuse.
- *Length.*—Approximately 2.0 cm.
- *Width.*—Approximately 0.5 cm.
- *Color.*—Upper surface at first opening: Near 187B. Upper surface at maturity: Near 46D. Upper surface at fading: Near 60A. Base of ray florets at first opening: Near 154B. Base of ray florets at maturity: Near 7A. Base of ray florets at fading: Near 15C. Under surface at first opening: Near 187D. Under surface at maturity: Near 186C. Under surface at fading: Near 186D.

Disc florets:
- *Appearance.*—Shiny.
- *Texture.*—Smooth.
- *Average number per flower.*—Approximately 10.
- *Shape.*—Cylindric.
- *Apex.*—Obtuse.
- *Average length.*—Approximately 0.4 cm.
- *Average width.*—Approximately 0.1 cm.
- *Color.*—At first opening: Near 154A. At maturity: Near 13A. At fading: Near 15A.

Peduncle:
- *Length.*—At terminal end (shortest): Approximately 3.4 cm. At lateral end (longest): Approximately 9 cm.
- *Angle to stem.*—Acute.
- *Strength.*—Moderate.
- *Color.*—Near 144A.
- *Habit.*—Upright.
- *Diameter.*—Approximately 0.2 cm.
- *Surface texture.*—Lightly pubescent.

Inflorescence bud:
- *Length.*—Approximately 0.6 cm.
- *Diameter.*—Approximately 1.0 cm.
- *Form.*—Globular.
- *Color.*—Near 187B when ray florets first emerge.

Involucral bracts (phyllaries):
- *Appearance.*—Matte.
- *Texture.*—Lightly pubescent.
- *Number.*—Approximately 109.
- *Shape.*—Oblanceolate.
- *Margin.*—Entire.
- *Apex.*—Acute.
- *Length.*—0.6 cm.
- *Width.*—0.3 cm.
- *Color.*—Upper side: Near 139B. Under side: Near 139B.

REPRODUCTIVE ORGANS

Ray florets:
- *Number of pistils per flower.*—1.
- *Stigma shape.*—2 branched.
- *Stigma color.*—Near 13A.
- *Style length.*—0.5 cm.
- *Style color.*—Near 154D.
- *Stamens.*—Absent.

Disc florets:
- *Number of pistils per flower.*—1.
- *Stigma shape.*—Two-branched.
- *Stigma color.*—Near 13A.
- *Style length.*—0.3 cm.
- *Style color.*—Near 154C.
- *Number of stamens per flower.*—5.
- *Anther shape.*—Tubular.
- *Anther color.*—Near 15A.
- *Pollen.*—No pollen detected.

OTHER CHARACTERISTICS

Seed production: Commercially, this plant is not used or observed in a stage wherein seeds would be produced. Therefore, seed production has not been observed.

Disease resistance: Neither resistance nor susceptibility to diseases and pests has been observed in this cultivar.

Heat and cold resistance: Plants with flowers are hardy to low temperatures about −2° C. Non flowering plants are hardy in the approximate range of 3° C. to −6° C., depending upon duration of cold and amount of moisture in the soil. With adequate water plants are hardy to a high temperature of 49° C.

What is claimed is:

1. A new and distinct cultivar of Chrysanthemum plant named 'Gedi Two Are' as herein illustrated and described.

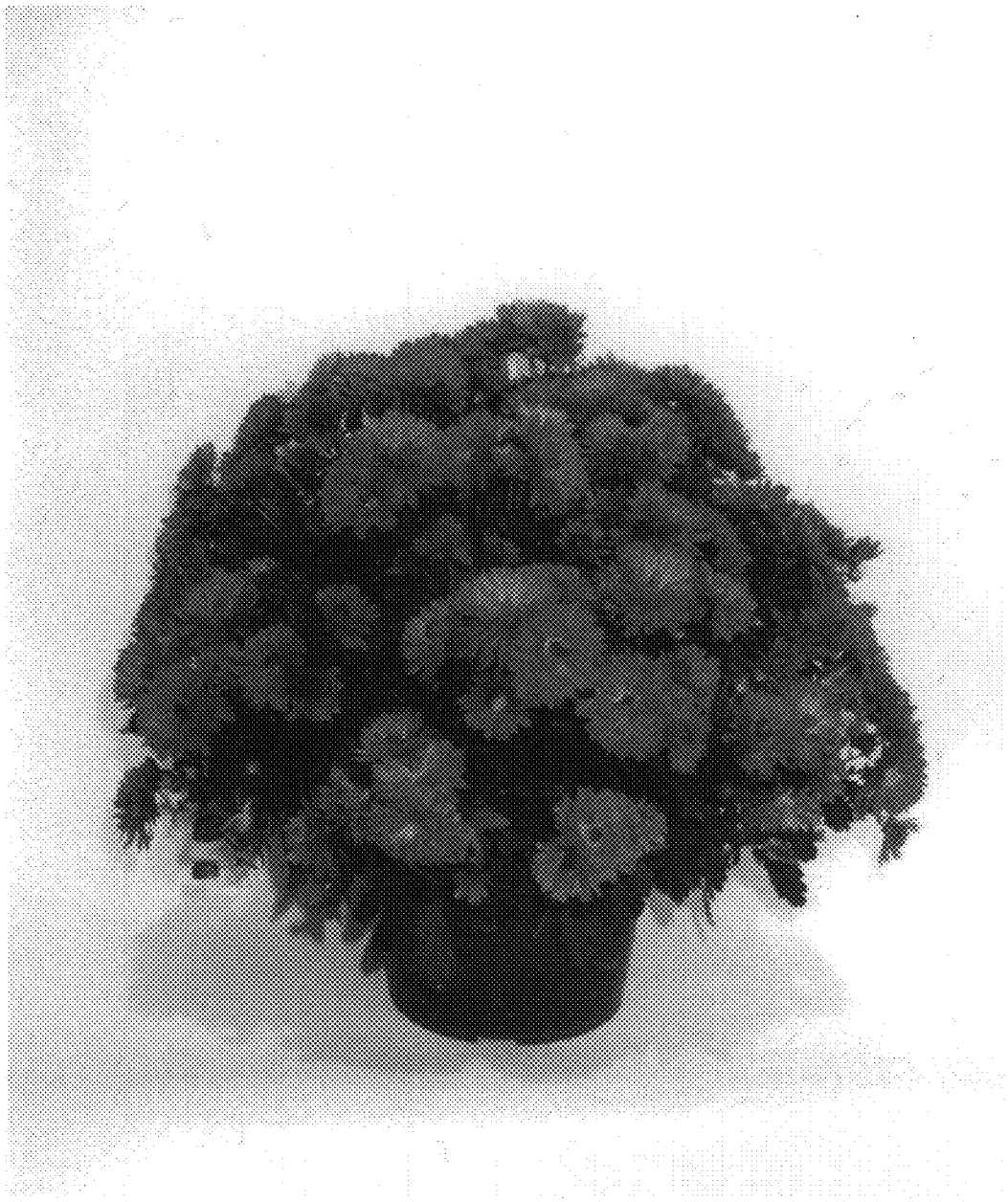

* * * * *